(12) United States Patent
Finger et al.

(10) Patent No.: US 10,166,143 B2
(45) Date of Patent: Jan. 1, 2019

(54) VERSATILE LIGHT-GUIDED OPHTHALMIC TREATMENT SYSTEM

(71) Applicant: IP LIBERTY VISION CORPORATION, New York, NY (US)

(72) Inventors: Paul T. Finger, New York, NY (US); Toby Welles, Redding, CT (US)

(73) Assignee: IP LIBERTY VISION CORPORATION, New York, NY (US)

( * ) Notice: Subject to any disclaimer, the term of this patent is extended or adjusted under 35 U.S.C. 154(b) by 468 days.

(21) Appl. No.: 14/243,629

(22) Filed: Apr. 2, 2014

(65) Prior Publication Data

US 2015/0182725 A1 Jul. 2, 2015

Related U.S. Application Data

(60) Provisional application No. 61/922,477, filed on Dec. 31, 2013.

(51) Int. Cl.
*A61M 25/01* (2006.01)
*A61N 5/10* (2006.01)
(Continued)

(52) U.S. Cl.
CPC .......... *A61F 9/0017* (2013.01); *A61N 5/1017* (2013.01); *A61B 2034/2055* (2016.02); *A61B 2090/3941* (2016.02); *A61B 2090/3945* (2016.02); *A61F 9/0079* (2013.01); *A61F 2009/00844* (2013.01); *A61N 5/062* (2013.01); *A61N 2005/1059* (2013.01); *Y10T 29/49826* (2015.01)

(58) Field of Classification Search
CPC .................. A61F 9/0017; A61F 9/0079; A61F 2009/00844; Y10T 29/49826; A61B 2034/2055; A61B 2090/3945; A61N 2005/1059; A61N 5/1017; A61N 5/062
See application file for complete search history.

(56) References Cited

U.S. PATENT DOCUMENTS 2,517,568 A 8/1950 Hissong
6,413,245 B1 7/2002 Yaacobi et al.
(Continued)

FOREIGN PATENT DOCUMENTS

WO WO 2009/009246 A1 1/2009
WO WO 2009/089288 A1 7/2009
WO WO 2014/074712 A2 5/2014

OTHER PUBLICATIONS

International Search Report for PCT Application No. PCT/US14/68472 dated Mar. 2, 2015.
(Continued)

*Primary Examiner* — Christine H Matthews
*Assistant Examiner* — Joshua D Lannu
(74) *Attorney, Agent, or Firm* — Smith Tempel; Steven P. Wigmore (57) ABSTRACT

A light-guided, ophthalmic-treatment-system for administering therapeutic agents to, into or through the scleral wall of the eye globe using any one of a variety of therapeutic applicators in conjunction with either transcorneal or transpupillary viewing methods or both.

15 Claims, 6 Drawing Sheets

(51) Int. Cl.
     *A61M 37/00*    (2006.01)
     *A61F 9/00*     (2006.01)
     *A61N 5/06*     (2006.01)
     A61F 9/007    (2006.01)
     A61F 9/008    (2006.01)
     A61B 34/20    (2016.01)
     A61B 90/00    (2016.01)

(56) References Cited

U.S. PATENT DOCUMENTS

| | | | |
|---|---|---|---|
| 6,443,881 B1* | 9/2002 | Finger | A61N 5/0601 600/1 |
| 6,491,618 B1* | 12/2002 | Ganz | A61B 18/24 600/3 |
| 2002/0087128 A1 | 7/2002 | Paques et al. | |
| 2004/0106904 A1* | 6/2004 | Gonnelli | A61B 17/205 604/173 |
| 2004/0138515 A1* | 7/2004 | White | A61N 5/1017 600/3 |
| 2004/0199130 A1* | 10/2004 | Chornenky | A61K 31/205 604/289 |
| 2005/0027156 A1 | 2/2005 | Pulido et al. | |
| 2007/0010746 A1 | 1/2007 | Forman et al. | |
| 2012/0209051 A1 | 8/2012 | Blumenkranz et al. | |
| 2013/0211178 A1 | 8/2013 | Brigatti et al. | |

OTHER PUBLICATIONS

Supplementary European Search Report for European Application No. 14877253.6 dated Sep. 12, 2017.

* cited by examiner

VERSATILE LIGHT-GUIDED OPHTHALMIC TREATMENT SYSTEM

CROSS REFERENCE TO RELATED APPLICATIONS

This application claims the benefit of U.S. Ser. No. 61/922,477, filed on Dec. 31, 2013, which is incorporated by reference herein in its entirety.

BACKGROUND OF THE INVENTION

The present invention relates to the administration of therapeutic agents into, on, or near the any portion of an eye globe, and specifically, relates to a light-guided, versatile delivery system employing any one of a variety of therapeutic applicators used in conjunction with transcorneal or transpupillary viewing methods.

BRIEF DESCRIPTION OF THE DRAWINGS

The subject matter regarded as the invention is particularly pointed out and distinctly claimed in the concluding portion of the specification. The features, their interaction, method of operation, and advantages may be understood with reference to the following detailed description in view of the accompanying drawings in which:

It will be appreciated that for clarity of illustration, device elements may be depicted in a manner not to scale, and reference numerals may be repeated among the figures to indicate corresponding elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. Well-known methods, procedures, and components have not been described in detail so as not to obscure the present invention.

The present invention relates to the delivery of therapeutic agents onto, into, or through the scleral wall of the eye, and specifically, relates to the use of various therapeutic applicators in conjunction with illumination markers facilitating placement in the desired location.

The following terms will used throughout the following document.

"Wand", "treatment wand" or "wand body" all refer to an elongated ergonomic and anatomically matching structure extending from a handle and supporting a therapeutic-agent applicator at its distal end. The wand is contoured to provide optimal access, visibility, and control, and fatigue-preventive ergonomics for the practitioner. In certain embodiments wand is implemented from a light transmissive material like, inter alia, polycarbonate, polysulfone and glass.

"Therapeutic-agent" refers to, inter alia, non-radioactive materials, drugs, excipients, cellular or cellular-byproduct materials, and drug-activating or remedial light. In modular applicator embodiments, therapeutic applicator may also be implemented as a radiation dispenser for administering radioactive materials as a therapeutic-agent.

"Illumination markers", "light markers", "light ports", "illumination ports" and "markers" all refer to light-based visual references either applied to a surface, embedded, or molded-in to portions of the wand or therapeutic applicator to assist a practitioner using transpupillary viewing methods to place the therapeutic applicator in a proper treatment position.

The term "luminescence" refers to emission of light through non-incandescent processes.

The term "fluorescence" refers to a type of photoluminescence in which the emission of electromagnetic radiation is released responsively to the absorption of incident radiation, the emission persisting only as long as the incident radiation is applied.

The term "phosphorescence" refers to a type of photoluminescence in which the emission of electromagnetic radiation is released responsively to the absorption of incident radiation and persists after removal of the incident radiation.

The term "chemiluminescence" refers to the emission of electromagnetic radiation responsively to a chemical reaction.

Figure 1A:
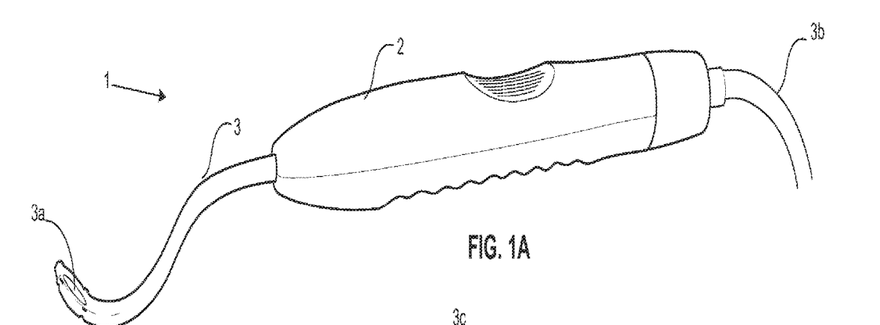
FIG. 1A is a schematic, perspective side-view of a light-guided, ophthalmic-treatment-device, according to an embodiment.
Figure 1B:
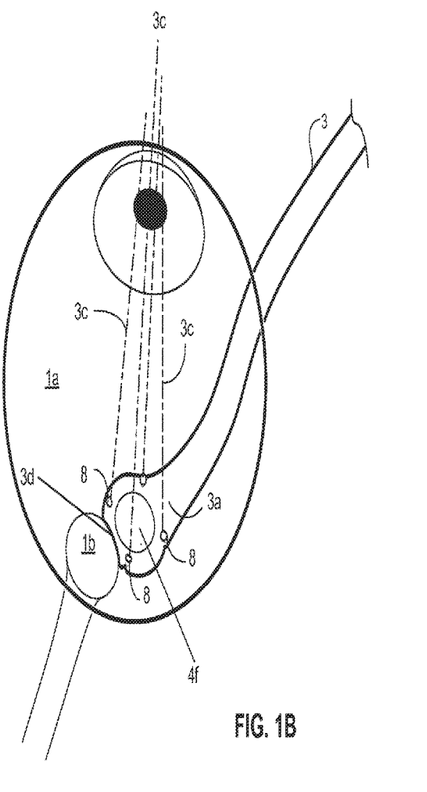
FIG. 1B is a schematic, perspective view of a light-guided, ophthalmic-treatment-device disposed in a treatment position behind an eye globe in which illumination ports are visible through transpupillary viewing techniques, according to an embodiment.

Turning now to the figures, FIGS. 1A and 1B depict a light-guided ophthalmic-treatment-device 1 configured to administer therapeutic agents onto, into, or through the scleral wall of the eye globe 1a by way of any one of a variety of therapeutic applicators 3a positioned near a distal end of a wand 3 held by a handle 2. As shown, the distal end of wand 3 exhibits an indentation 3d facilitating abutment with an optic nerve sheath 1b or other anatomical features having a similar surface profile.

The ophthalmic-treatment-device 1 includes a plurality of illumination markers 8 defining a line circumscribing therapeutic applicators 3a and therapeutic agent 4f delivered though it, according to an embodiment. Transpupillary viewing methods enable practitioners to use light emissions 3c from light markers 8 to facilitate placement of medicament dispenser 3a in a treatment area. Transcorneal or transpupillary viewing methods include, inter alia, observation, ophthalmoscopy, optical coherence tomography and videography.

Illumination markers 8 may emit either light propagating through wand 3 from an external light source 3b, as shown, or alternatively generate their own luminescence from either photoluminescent materials from which markers 8 are constructed or electroluminescent or chemiluminescent material contained within markers 8, according to embodiments. It should be appreciated that in certain embodiments photoluminescent materials are excited from a light source embedded in wand 3 or applicator 3a while in other embodiments the excitation light source is disposed outside wand body 3.

Examples of suitable photoluminescent materials include, inter alia, strontium aluminate based pigments for phosphorescent illumination markers and fluorescein for fluorescent illumination markers. It should be appreciated that other materials exhibiting such functionality are included within the scope of the present invention.

Photoluminescent materials of light markers 8 may either be applied to a surface, embedded, or molded-in to portions of the wand or the therapeutic applicator, according to embodiments.

Photoluminescent illumination markers may be excited by either ultra violet (UV) light or any of various frequencies of electromagnetic radiation such as radio waves, microwave, infrared, visible light, x-ray, or gamma rays and also particle radiation like beta particles or other charged particles. Examples of electroluminescent illumination markers include, inter alia, light emitting diodes or organic light emitting diodes disposed in illumination markers 8.

Chemiluminescent markers 8 may be activated through a chemical reaction of chemiluminescent reactants mixing either within a wand or applicator chamber or mixing externally and fed into therapeutic applicator. Examples of suitable reactants include highly oxidized molecules, such as peroxide, and luminol, $C_8H_7N_3O_2$, or diphenyl oxalate, $C_{14}H_{10}O_4$. It should be appreciated that other reactants exhibiting such chemiluminescent functionality are also included within the scope of the present invention.

Figure 2A:
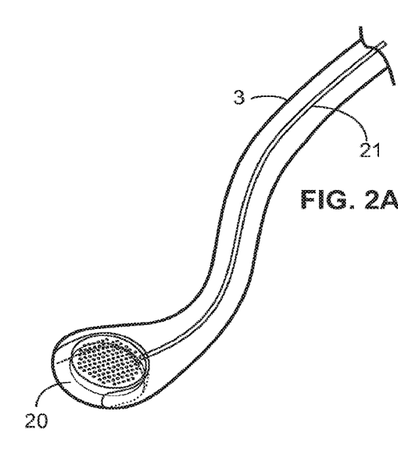
FIG. 2A is a schematic, perspective view of a light-guided, ophthalmic-treatment-wand having a therapeutic applicator implemented as perforated dispenser, according to an embodiment.

FIG. 2A depicts a treatment wand 3 of a light-guided, ophthalmic-treatment-device having a therapeutic applicator implemented as a perforated head 20 through which therapeutic agents fed through feed line 21 are expelled when disposed in a treatment position. It should be appreciated that various perforation patterns and shapes are included within the scope of the present invention.

Figure 2B:
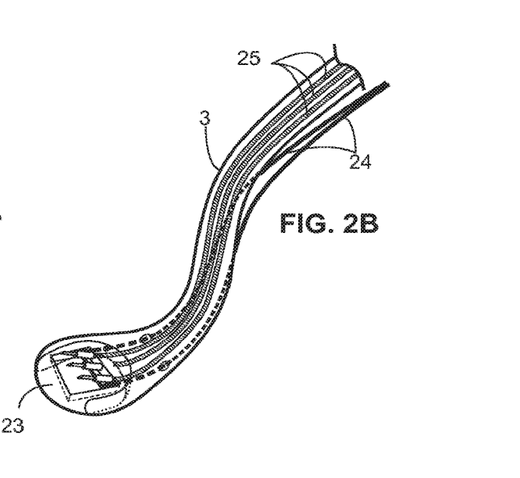
FIG. 2B is a schematic, perspective view of a light-guided, ophthalmic-treatment-wand having a therapeutic applicator implemented as an injector array, according to an embodiment.

FIG. 2B depicts a treatment wand 3 of a light-guided, ophthalmic-treatment-device having a therapeutic applicator implemented as an injection array 23 configured to inject various therapeutic agents fed through feed lines 25 when disposed in a treatment position, according to an embodiment.

Injection array 23 is pivotally mounted and biased to assume a non-protruding orientation when in a non-injection position and may be pivoted into an injection position by pulling on control cords or rods 24 when disposed in a treatment position, according to an embodiment.

In a certain embodiment, the injector array is implemented as a non-pivotal, retractable array configured to advance and to retract responsively to expansion and deflation of pneumatic or hydraulic devices as is known to those skilled in the art.

Furthermore, injector array advancement and retraction may be achieved through various ramping arrangements also as is known to those skilled in the art.

It should be noted that arrays implemented with a single injection needle are also included within the scope of the present invention.

Figure 2C:
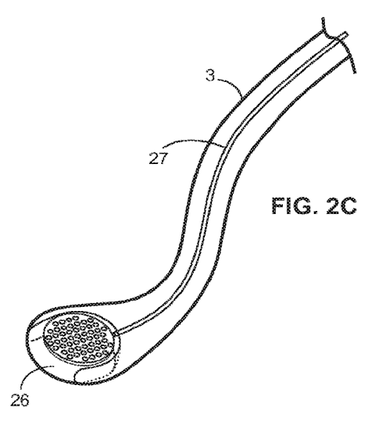
FIG. 2C is a schematic, perspective view of a light-guided, ophthalmic-treatment-wand having a therapeutic applicator implemented as a treatment-light array, according to an embodiment.

FIG. 2C depicts a treatment wand 3 of a light-guided ophthalmic-treatment-device having a therapeutic applicator implemented as a drug actuating or therapeutic light array 26. In a certain embodiment, light array 26 is implemented as a laser array; however, it should be appreciated that other light emitting sources providing the same functionally are also included within the scope of the present invention. Power may be supplied through a wand slot 51 shown in FIG. 5A, according to an embodiment.

It should be further appreciated that in certain embodiments, the therapeutic applicator is implemented as a reflector arrangement configured to direct a drug-activation light or therapeutic light that are generated externally and propagated through fiber optic 27. Such a therapeutic applicator is also included within the scope of the present invention.

Figure 2D:
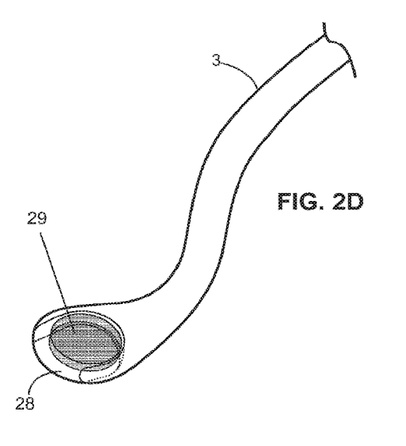
FIG. 2D is a schematic, perspective view of a light-guided, ophthalmic-treatment-wand having a therapeutic applicator implemented as a shielded container for radioactive therapeutics, according to an embodiment.

FIG. 2D depicts a treatment wand 3 of a light-guided, ophthalmic-treatment-device having a therapeutic applicator implemented as a shielded container 28 for holding radioactive therapeutics 29, according to an embodiment. Container materials may include selective radiation shielding materials known to those skilled in the art.

Figure 3A:
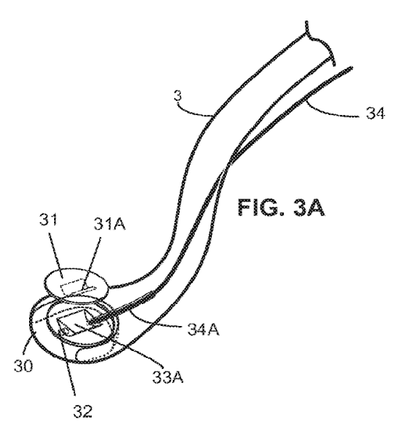
FIG. 3A is a schematic, perspective view of a light-guided, ophthalmic-treatment-wand having a therapeutic applicator implemented as an medicated-adhesive-patch applicator, according to an embodiment.

FIG. 3A depicts a treatment wand 3 of a light-guided ophthalmic-treatment-device having a therapeutic applicator implemented as a medicated-adhesive-patch applicator 30, according to an embodiment. Shown in a disengaged state, patch 31 has an engagement sleeve or passageway 31A disposed on the non-adhesive side. Therapeutic applicator 30 includes a patch receptacle 33A having openings 32 in facing walls so as to enable selective disengagement by wire 34 traversing both receptacle 33A and engagement sleeve 31A when patch 31 is seated in receptacle 33A. Release wire 34 is slideably mounted in sleeve 34A disposed in wand 3, according to an embodiment.

Figure 3B:
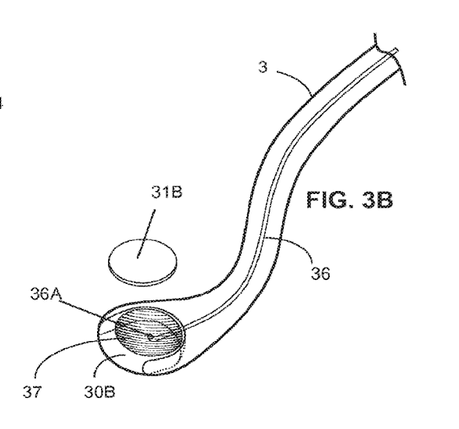
FIG. 3B is a schematic, perspective view of a light-guided, ophthalmic-treatment-wand having a therapeutic applicator implemented as a suction-based applicator for medicated-adhesive-patch, according to an embodiment.

FIG. 3B depicts a treatment wand 3 of a light-guided ophthalmic-treatment-device having a therapeutic applicator implemented as a suction-based applicator 30B for medicated-adhesive-patch 31B, according to an embodiment.

Shown in a disengaged state, patch 31B is releasably held to applicator 30B on a generally flat or concave support surface 37 having an orifice in communication with a tubule 36 traversing the length of the wand. During operation, suction is applied to tubule 36 so as to hold medicated-adhesive-patch 31B on support surface 37 until the suction is removed when medicated-adhesive-patch 31B is disposed and secured on the target tissue with adhesive, according to an embodiment.

Figure 3C:
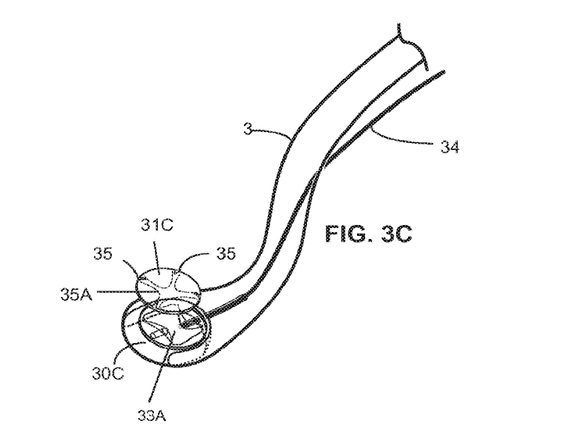
FIG. 3C is a schematic, perspective view of a light-guided, ophthalmic-treatment-wand having a therapeutic applicator implemented as a medicated-spurred-patch applicator, according to an embodiment.

FIG. 3C depicts a treatment wand 3 of a light-guided ophthalmic-treatment-device having a therapeutic applicator implemented as a medicated-spur-patch applicator 30C for mechanical attachment of medicated patches, according to an embodiment.

Medicated patch 31C is fitted with a series of circumferentially-spaced, radially-disposed spurs 35, each one connected to a radial strip emanating from a single engagement patch 35 disposed on the non-medicated side of patch 31C. Patch dispenser 30C includes a patch receptacle 33A analogous to the one described above. When medicated patch 31C is seated in receptacle 33A and wire 34 traverses receptacle 33A between medicated patch 31C and its engagement patch 35, wire 34 pulls engagement strap 35 away from medicated patch 31C thereby rotating spurs 35 outward into a protruding orientation so as to enable penetration into tissue when pressure is applied.

Upon extraction of wire 34, the spur-rotating-force is removed enabling patch 31C, biased to resume its original flat disposition, to apply a counter torque to the now embedded spurs to resume their original radial disposition thereby causing them to engage the tissue and hold medicated patch 31B in place, according to an embodiment.

It should be appreciated that these configurations are only examples, and other configurations providing spur engagement functionality are included within the scope of the present invention.

Figure 4A:
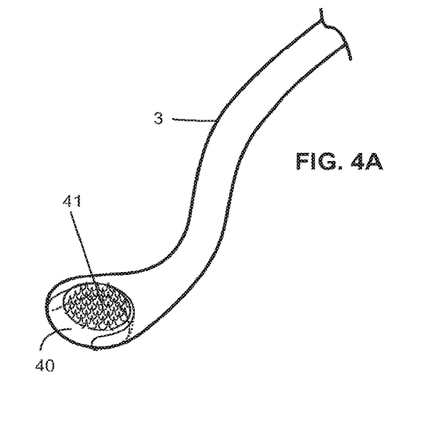
FIG. 4A is a schematic perspective view of a light-guided, ophthalmic-treatment-wand having a therapeutic applicator implemented as a drug-coated, micro-needle array, according to an embodiment.

FIG. 4A depicts a treatment wand 3 of a light-guided ophthalmic-treatment-device having a therapeutic applicator implemented as a micro-needle array 40 of drug-coated micro needles 41, according to an embodiment.

Figure 4B:
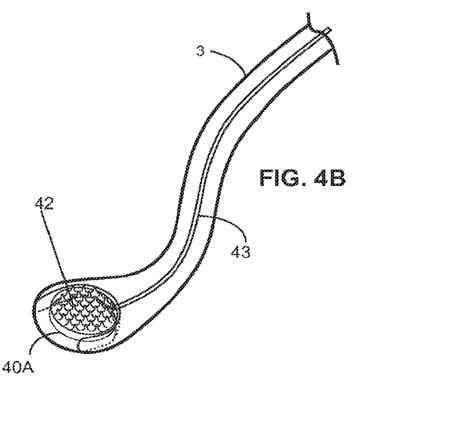
FIG. 4B is schematic perspective view of a light-guided, ophthalmic-treatment-wand having a therapeutic applicator implemented as a micro-needle array of hollow micro-needles, according to an embodiment.

FIG. 4B depicts a treatment wand 3 of a ophthalmic-treatment-device having a therapeutic applicator implemented as a micro-needle array 40A of hollow micro-needles 42 fed from feed line 43 disposed in wand 3, according to an embodiment.

Figure 4C:
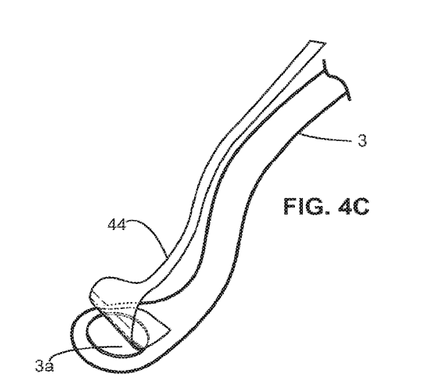
FIG. 4C is schematic perspective view of a light-guided, ophthalmic-treatment-wand fitted with a removable therapeutic-applicator-cover, according to an embodiment.
Figure 4D:
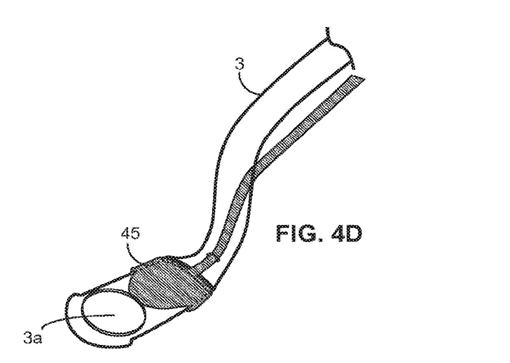
FIG. 4D is schematic perspective view of a light-guided, ophthalmic-treatment-wand fitted with a slideable therapeutic-applicator-cover, according to an embodiment.

FIGS. 4C and 4D depicts a treatment wand 3 of a light-guided, ophthalmic-treatment-device fitted with an therapeutic-applicator cover configured to prevent inadvertent damage to a patient or the therapeutic applicator 3a and to also prevent premature or misdirected therapeutic administration during insertion or removal of the device.

Specifically, FIG. 4C depicts a peelable, therapeutic-applicator cover 44 removably attached to therapeutic applicator 3a and wand 3 according to an embodiment. Peelable, therapeutic-applicator cover 44 is constructed from a polymeric sheet and coated with an adhesive material as is known to those skilled in the art. In practice, a practitioner unpeels cover 44 by pulling on its proximal end after therapeutic applicator 3a is disposed in a treatment position.

FIG. 4D depicts a slideable, therapeutic-applicator cover 45 slideably attached to wand 3 according to an embodiment. As shown, therapeutic-applicator cover 45 shields therapeutic applicator 3a and traverses wand 3 so as to enable a practitioner to reveal therapeutic applicator 3a by pulling on a proximal portion of cover when disposed in a treatment position, according to an embodiment.

Figure 5A:
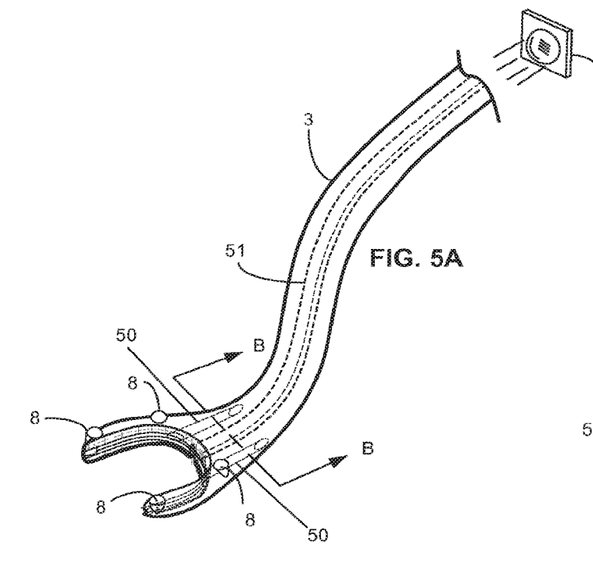
FIG. 5A is a schematic, perspective view of a standard light-guided ophthalmic-treatment-wand of a modular embodiment depicting a multi-use slot and lumens, and a standard connection configuration, according to an embodiment.
Figure 5B:
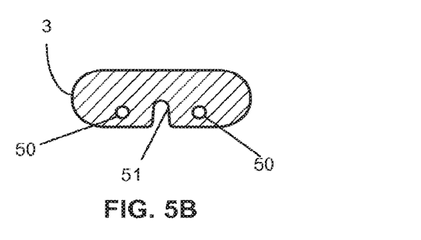
FIG. 5B is a sectional view of the standard ophthalmic-treatment-wand of FIG. 5A, according to an embodiment

FIG. 5A and sectional view FIG. 5B along B-B depict a standard wand 3 configured to receive any one of the above described therapeutic applicators 3a implemented modularly. In a certain embodiment, wand 3 has a wand slot 51 for receiving various service lines for the therapeutic applicator 3a like, inter alia, feed lines of therapeutic agents, power lines for driving light arrays, and fiber optics directing externally generated light. Furthermore, modular wand 3 has service lumens 50 for receiving control cords or rods used to actuate or change a disposition of therapeutic applicator 3a or a component of it. As noted above, wand 3 also includes illumination markers 8 providing visual markers that may be implemented as either a luminescent illumination marker 8 upon excitation or an emission port for externally generated light 6 propagating through a light transmissive wand, according to embodiments. Furthermore, in a modular embodiment, wand 3 has connection configuration common to a variety of therapeutic applicators 3a thereby advantageously enabling any one of them having a corresponding connection configuration to be connected to wand 3.

Figures 5C, 5D:
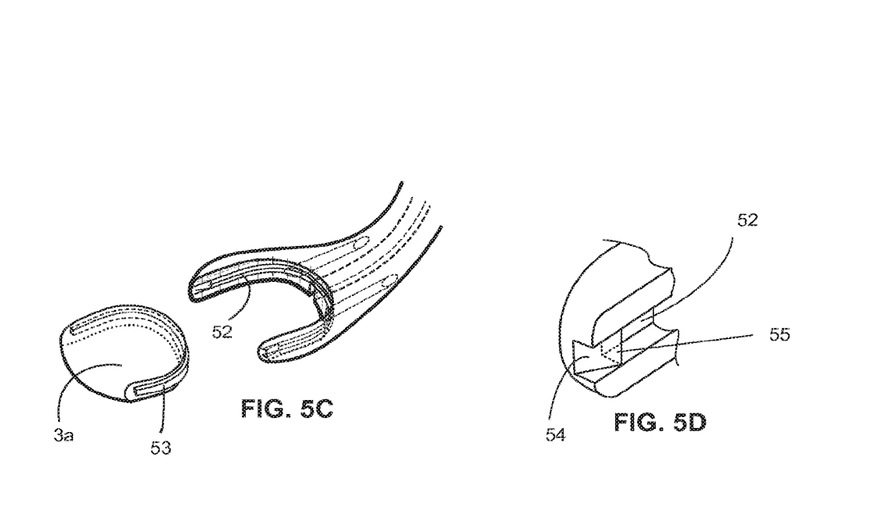
FIG. 5C is an enlarged, schematic-perspective view of the engagement configuration of the wand of FIG. 5B and a therapeutic applicator, according to an embodiment.
FIG. 5D is an enlarged, schematic-perspective view of a catch mechanism of connection configuration of FIG. 5B, according to an embodiment.

FIGS. 5C and 5D depicts a sample connection configuration for modular therapeutic applicators 3a and standard wand 3, according to an embodiment. As shown, therapeutic applicator 3a has a ridge 53 corresponding to a mating groove 52 disposed along the distal end of wand 3. Ramps 54 disposed at both ends of groove 52 gradually negate the groove depth and at the point in which the groove depth is entirely negated the ramps abruptly terminate and have a non-ramped face 55 which acts as a catch against each end of ridge 53 when slid into groove 52, according to an embodiment. It should be appreciated that thread arrangements and other connection configurations providing selectable engagement are included within the scope of the present invention.

Figure 6:
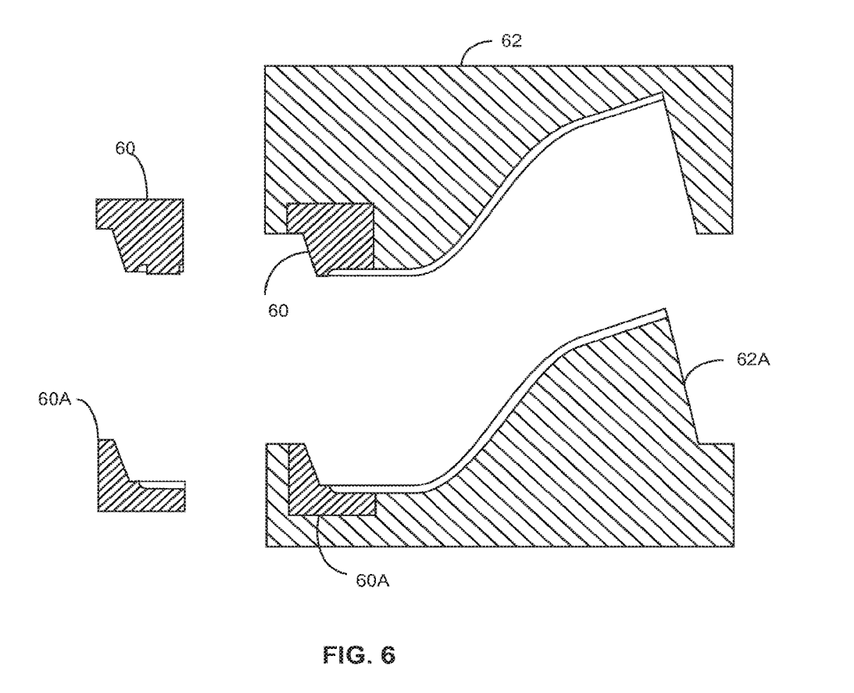
FIG. 6 is a schematic, sectional view of a mold and interchangeable mold insert employed in the manufacture of an ophthalmic-treatment-wand and various molded-on therapeutic applicators, according to an embodiment.

FIG. 6 depicts an exchangeable insert mold 60 and 60A for construction of various therapeutic applicators and a wand mold 62 and 62A, according to an embodiment. Specifically, each exchangeable mold insert 60 and 60A is dedicated to a therapeutic applicator and upon molding of a particular therapeutic applicator, the corresponding insert mold 60 and 60A is inserted into wand mold 62 and 62A so as to integrally connect the selected therapeutic applicator with the distal portion of the wand during molding, according to an embodiment.

It should be appreciated that any combination of features set forth in particular embodiments and multimodal therapeutic applicators are included within the scope of the present invention. "Multimodal therapeutic applicators" employ different applicator types either simultaneously or non-simultaneously.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A light-guided, ophthalmic-treatment device comprising:

an ophthalmic treatment wand having a body made of light transmissive material, said ophthalmic treatment wand having a distal end;
a therapeutic applicator held at the distal end of the ophthalmic treatment wand; and
a plurality of emission ports at least partially circumscribing the therapeutic applicator;
wherein said ophthalmic treatment wand is configured to propagate light through the body to the plurality of emission ports.

2. The device of claim 1, wherein the therapeutic applicator is selected from the group consisting of a perforated dispenser, medicated-patch applicator, treatment-light array, and needle array.

3. The device of claim 2, wherein the medicated patch applicator includes an adhesive-patch applicator.

4. The device of claim 2, wherein the needle array includes drug-coated micro-needles or hollow micro-needles.

5. The device of claim 1, wherein the emission ports include luminescent markers selected from the group consisting of photoluminescent markers, electroluminescence markers, and chemiluminescent markers.

6. The device of claim 1, wherein the ophthalmic treatment wand includes an applicator cover.

7. The device of claim 6, wherein the applicator cover is configured to be removed from the wand.

8. A modular, light-guided ophthalmic-treatment-system comprising:
an ophthalmic-treatment wand, said wand having a body having a plurality of illumination markers at least partially circumscribing an interchangeable therapeutic applicator when attached to the wand; and
a plurality of modular interchangeable therapeutic applicators, each of the applicators releasably connectable with the wand, each applicator embodying a different therapeutic agent delivery configuration operative to administer a therapeutic agent suitable for each respective delivery configuration when any one of the plurality of modular interchangeable therapeutic applicators in one of the plurality of delivery configurations is connected to the wand and loaded with the suitable therapeutic agent.

9. The ophthalmic-treatment-system of claim 8, wherein each of the plurality of the modular therapeutic applicators is selected from the group consisting of a perforated dispenser, a medicated-patch applicator, a treatment-light array, a injector array, a micro-needle array, and a radioactive-therapeutic container.

10. The ophthalmic-treatment-system of claim 8, wherein the ophthalmic-treatment wand includes a light transmissive wand.

11. The ophthalmic-treatment-system of claim 8, wherein the illumination markers include luminescent markers selected from the group consisting of photoluminescent markers, chemiluminescent markers, and electroluminescence markers.

12. The ophthalmic-treatment-system of claim 8, wherein the ophthalmic-treatment wand includes a therapeutic applicator cover.

13. A method for constructing a modular, light-guided ophthalmic-treatment-system comprising:
providing an ophthalmic treatment wand made of a light transmissive material, said wand having a distal end, and a therapeutic applicator with a plurality of emission ports at least partially circumscribing said therapeutic applicator, said wand is configured to propagate light through the wand to the plurality of emission ports at least partially circumscribing the therapeutic applicator when held at the distal end of the wand; and
releasably connecting the therapeutic applicator to the distal end of the wand.

14. The method of claim 13, wherein the therapeutic applicator is selected from the group consisting of a perforated dispenser, a medicated-patch applicator, a treatment-light array, an injector-array, a micro-needle array, and a radioactive-therapeutic container.

15. The method of claim 13, wherein the ophthalmic treatment wand includes a therapeutic applicator cover.

\* \* \* \* \*